United States Patent [19]

Theissen

[11] Patent Number: 4,633,000
[45] Date of Patent: Dec. 30, 1986

[54] 2-NITRO-5-(SUBSTITUTED-PHENOXY) PHENYLALKANONE OXIME AND IMINE DERIVATIVES AS HERBICIDES

[75] Inventor: Robert J. Theissen, Bridgewater, N.J.

[73] Assignee: Rhone Poulenc Agrochimie, Lyons, France

[21] Appl. No.: 620,480

[22] Filed: Jun. 14, 1984

Related U.S. Application Data

[62] Division of Ser. No. 117,731, Feb. 1, 1980, Pat. No. 4,551,171.

[51] Int. Cl.⁴ .................... C07D 303/08; C07C 79/46; C07C 131/00

[52] U.S. Cl. ....................................... 549/551; 560/21; 564/255

[58] Field of Search ............................ 564/255; 560/21; 549/551; 260/465 D

[56] References Cited

U.S. PATENT DOCUMENTS 4,344,789  8/1982  Krass ..................................... 560/21
4,490,167  12/1984  Pissiotas et al. ................. 260/465 D Primary Examiner—Delbert R. Phillips
Attorney, Agent, or Firm—Morgan & Finnegan

[57] ABSTRACT

There is provided a new class of derivatives of 2-nitro-5-(substituted-phenoxy) phenylalkanone oximes and imines that have pre- and post-emergence herbicidal activity.

4 Claims, No Drawings

2-NITRO-5-(SUBSTITUTED-PHENOXY) PHENYLALKANONE OXIME AND IMINE DERIVATIVES AS HERBICIDES

The present application is a division of application Ser. No. 117,731 filed Feb. 1, 1980 and is now U.S. Pat. No. 455,171, before the Patent Office.

FIELD OF THE INVENTION

This invention is concerned with herbicidal 2-nitro-5-(substituted-phenoxy)phenylalkanone oxime and imine derivatives.

CROSS REFERENCES TO RELATED APPLICATIONS

Applicant Theissen herein has been granted a series of patents relating to 2-nitro-5-(substituted-phenoxy)-benzoic acid derivatives including the salt, alkyl and cycloalkyl esters, alkylthio esters, phenyl ester, alkyl and dialkyl amido and benzoyl chloride forms. Illustrative of those patents are U.S. Pat. Nos. 3,652,645; 3,784,635; 3,873,302; 3,983,168 and 3,907,866.

BRIEF SUMMARY OF THE INVENTION

This invention provides certain herbicidal compounds falling within the general formula:

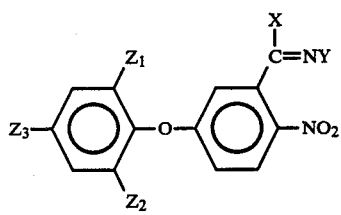

wherein
$Z_1$ is halogen,
$Z_2$ is selected from halogen and hydrogen, and
$Z_3$ is a polyhalo$_{1-9}$ alkyl$_{1-4}$ group such as $CF_3$, $CHF_2$, $C_4F_9$, $CF_2CH_2CH_3$ and $CH_2Cl$.
X is selected from the group consisting of hydrogen, cyano, alkoxy of 1 to 6 carbons, alkyl of 1 to 6 carbons.
Y is selected from the group consisting of hydroxy, alkali metal oxide (e.g., —ONa, —OK), N-alkylaminocarboxy and N,N-dialkylaminocarboxy where each alkyl group is of 1 to 6 carbons, 1-(alkoxycarbonyl)alkoxy where each alkoxy is of 1 to 6 carbons, alkyl of 1 to 6 carbons, epoxyalkoxy where the alkoxy is of 3 to 6 carbons.

The alkyl and alkoxy groups referred to herein may be of branched or straight carbon chains.

In accordance with the foregoing formula, preferable substituents include $Z_1$ is chloro, $Z_3$ is $CF_3$ and $Z_2$ is hydrogen.

DETAILED DESCRIPTION

The specific 2-nitro-5-(substituted-phenoxy)phenyl alkanone derivatives are described below. One method for preparing these compounds is the use of the Ullmann ether synthesis reaction between the alkali metal (e.g., Na, K) salt of a suitable substituted phenol, e.g., m-hydroxy benzaldehyde or m-cresol with an active halogen-substituted aromatic, e.g., 3,4-dichlorobenzotrifluoride. The intermediate obtained may be nitrated and subsequently derivatized by known procedures. Where m-cresol is used as a starting material, the product obtained can be oxidized and subsequently nitrated before the aforementioned derivatization.

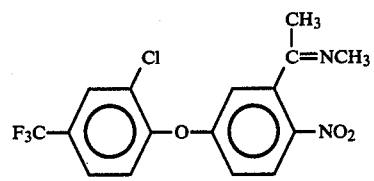

Compound 1

Preparation of 5-[2-chloro-4-(trifluoromethyl)-phenoxy]-2-nitrophenyl ethanone methylimine.

To a stirred solution of 5-[2-chloro-4-(trifluoromethyl)phenoxy]-2-nitrophenyl ethanone (3.3 g., 0.0092 mole) in absolute ethanol (30 ml) was bubbled methylamine for 0.5 hour as the temperature rose to about 40° C. The solution was stirred for 12 hours at room temperature and then heated to reflux for 4 hours. The solvent was stripped to give 3.0 g of a brown oil. Recrystallization from methanol/water gave a brown solid (1.2 g., mp. 133°–7° C.).

I.R. (nujol): C=O absent.

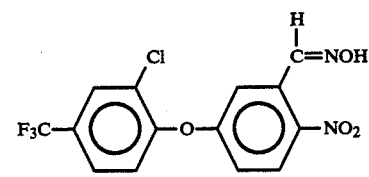

Compound 2

Preparation of 5-[2-chloro-4-(trifluoromethyl)-phenoxy]2-nitrobenzaldehyde oxime.

To a solution of hydroxylamine hydrochloride (0.33 g., 0.0048 mole) and sodium acetate (0.394 g., 0.0048 mole) in 2–3 ml of water was added a hot solution of 5-[2-chloro-4-(trifluoromethyl)phenoxy]-2-nitrobenzaldehyde (1.5 g., 0.00434 mole) in ethanol (10–12 ml). The clear yellow solution was heated for 1.5 hours and then the solvent was stripped on a rotary evaporator to give a yellow waxy solid which solidified giving 1.5 g., mp. 111°–115° C. Recrystallization from ethanol/water gave a solid mp. 114°–118° C.

I.R. (KBr): C=O absent.

NMR (CDCl$_3$): Singlet 8.85 ppm (1H); Doublet 8.30 ppm (J=4.5 Hz, 1H); Complex multiplet 7.0–8.0 ppm (7H).

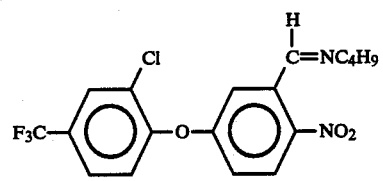

Compound 3

5-[2-chloro-4-(trifluoromethyl)phenoxy]-2-nitrobenzaldehyde t-butylimine was prepared in a manner similar to that shown for Compound 1. The product was an oily semi-solid.

I.R. (neat): C=O absent.

NMR (CDCl$_3$): Singlet 1.34 ppm (9H); Complex multiplet 6.9–8.4 ppm (6H); Singlet 8.9 ppm (1H).

Other illustrative compounds of the present invention are shown below in accordance with the following formula:

| X | Y | Name |
|---|---|---|
| H | —ONa | 5-[2-chloro-4-(trifluoromethyl) phenoxy]-2-nitrobenzaldehyde oxime sodium salt |
| H | —OCNHCH$_3$ (with C=O) | 5-[2-chloro-4-(trifluoromethyl) phenoxy]-2-nitrobenzaldehyde methylaminocarbonyloxime |
| H | —OCHCOCH$_3$ \| CH$_3$ (with C=O) | 5-[2 chloro-4-(trifluoromethyl) phenoxy]-2-nitrobenzaldehyde 1-(methoxycarbonyl) ethyloxime |
| —CN | OC—N(CH$_3$)$_2$ (with C=O) | 5-[2-chloro-4-(trifluoromethyl) phenoxy] α-cyano-2-nitro-benzaldehyde (N,N—dimethyl-aminocarbonyl) oxime |
| —OC$_2$H$_5$ | —OCH$_2$CH—CH$_2$ (with O bridge, epoxide) | ethyl O—(2,3-epoxy propyl) 5-[2-chloro-4-(trifluoromethyl) phenoxy]-2-nitro-benzohydroximate |

PRIMARY HERBICIDE SCREENING

The compounds of this invention can be applied in various ways to achieve herbicidal action. They can be applied per se, as solids or in vaporized form, but are preferably applied as the toxic components in pesticidal compositions of the compound and a carrier. These compositions are preferably applied directly to the soil and often incorporated therewith. The compositions can be applied as granulars or dusts; as liquid sprays, or as gas-propelled sprays and can contain, in addition to a carrier, additives such as emulsifying agents, binding agents, gases compressed to the liquid state, odorants, stabilizers, and the like. A wide variety of liquid and solid carriers can be used. Non-limiting examples of solid carriers include talc, bentonite, diatomaceous earth, pyrophyllite, fullers earth, gypsum, flours derived from cotton seeds and nut shells, and various natural and synthetic clays having a pH not exceeding about 9.5. Non-limiting examples of liquid carriers include water, organic solvents such as alcohols, ketones, light oils, and medium oils and vegetable oils such as cottonseed oil.

In practice, herbicidal application is measured in terms of pounds of herbicide applied per acre. The compounds of this invention are effective herbicides when applied in herbicidal amounts, i.e., at rates between about 0.03 pound and about 10 pounds per acre.

HERBICIDAL EFFECTIVENESS

Method of Propagating Test Species

Crop and weed species are planted in 8"×10" disposable fiber flats containing potting soil to provide each flat with a 4" row of all test species. Crop species consist of field corn (CN), crabgrass (CG), cotton (CT), and soybeans (SB). The weed species consist of foxtail millet (FM), green foxtail (GF), velvetleaf (VL), cocklebur (CB), wild mustard (WM) and pigweed (PW).

Cotton, corn, soybean, and cocklebur plantings consist of 4 to 5 seeds per row depending upon species. The smaller seeded species (velvetleaf, wild mustard, pigweed, foxtail millet and green foxtail) are planted in an uncounted but sufficient number to provide a solid row of seedlings.

Plantings for the pre- and post-emergence portions of the test are identical as to seeding. The initial watering until emergence is done from the top. The post-emergence phase is propagated in advance so as to provide plants of the proper stage of development at the time of treatment. Plantings for the pre-emergence phase are made not more than one day in advance of treatment.

The desired stage of development for treatment of the post-emergence broadleaf species (CT, SB, CB, VL, WM, PW) is the one true leaf or first trifoliate leaf stage. The desired stage for corn would be a height of 3-4", while a 2" height would be adequate for the grasses.

Method of Treatment

Spray applications are made with a handgun sprayer (aspirator type) simultaneously to one flat of established plants for the post-emergence phase and one newly seeded flat for the pre-emergence phase. The 10 lb./acre treatment rate consists of the uniform application of 116 milligrams of test compound to the combined area of the two flats (160 sq. inches). Application is made in a solvent mixture consisting of 40 ml acetone and 40 ml water and a surfactant concentration of 0.1%, Following spray application, flats are returned to the greenhouse where watering of the post-emergence phase is done only by subirrigation. The pre-emergence phase is top watered by sprinkling until after test species have emerged. Subsequent watering is by subirrigation.

Two weeks after treatment, the pre- and post-emergence injury and control is rated on a 0-100% injury and control scale. Special physiological effects are rated as to intensity also at this time.

The herbicidal test data reported for compounds 1-3 was obtained at application rates of 2 lbs. down to ¼ lb./acre. The following lists the metric equivalents for each rate.

| Application Rate | |
|---|---|
| US - lb./acre | Metric - kg/ha |
| 2.0 | 2.24 |
| 0.5 | 0.56 |
| 0.25 | 0.28 |

Test results are set forth in Table I (pre-emergence) and Table II (post-emergence).

TABLE I

| Cpd. No. | Dosage Lbs./Acre | CG | FM | GF | VL | CB | WM | PW | CT | CN | SB |
|---|---|---|---|---|---|---|---|---|---|---|---|
| 1 | 2 | 50 | 10 | — | 0 | 10 | 30 | — | — | — | — |
|  | ¼ | 0 | 0 | — | 0 | 0 | 0 | — | — | — | — |

TABLE I-continued

| Cpd. No. | Dosage Lbs./Acre | Pre-Emergence | | | | | | | | | |
|---|---|---|---|---|---|---|---|---|---|---|---|
| | | CG | FM | GF | VL | CB | WM | PW | CT | CN | SB |
| 2 | 2 | — | 90 | 90 | 70 | 0 | 90 | 80 | 10 | 0 | 0 |
| | ½ | — | 70 | 0 | 20 | 0 | 20 | 20 | 0 | 0 | 0 |
| 3 | 2 | — | 80 | 60 | 10 | 10 | 90 | 100 | 20 | 10 | 0 |
| | ½ | — | 20 | 20 | 0 | 0 | 10 | 70 | 0 | 0 | 0 |

TABLE II

| Cpd. No. | Dosage Lbs./Acre | Post-Emergence | | | | | | | | | |
|---|---|---|---|---|---|---|---|---|---|---|---|
| | | CG | FM | GF | VL | CB | WM | PW | CT | CN | SB |
| 1 | 2 | 60 | 50 | — | 90 | 40 | 80 | 100 | 90 | 10 | 30 |
| | ½ | 10 | 70 | — | 10 | 10 | 40 | 100 | 40 | 10 | 10 |
| 2 | 2 | 20 | 50 | — | 100 | 70 | 90 | 100 | 80 | 10 | 50 |
| | ½ | 10 | 10 | — | 100 | 10 | 90 | 80 | 30 | 10 | 30 |
| 3 | 2 | — | 90 | 90 | 70 | 10 | 100 | 100 | 70 | 50 | 50 |
| | ½ | — | 60 | 60 | 10 | 10 | 90 | 90 | 50 | 10 | 40 |
| | ¼ | — | 60 | 40 | 50 | 20 | 90 | 70 | 30 | 20 | 20 |

What is claimed is:

1. Herbicidal compounds of the formula:

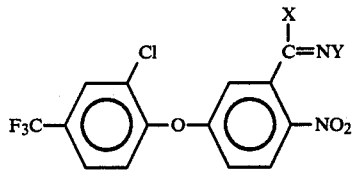

wherein:

X is selected from the group consisting of hydrogen, alkoxy of 1 to 6 carbons, alkyl of 1 to 6 carbons;

Y is selected from the group consisting of N-alkylaminocarboxy and N,N-dialkylaminocarboxy where each alkyl group is of 1 to 6 carbons, epoxyalkoxy where the alkoxy is of 3 to 6 carbons.

2. The compounds of claim 1 wherein Y is selected from N-alkylamino carboxy and N,N-dialkylamino carboxy where each alkyl group is of one to six carbon atoms.

3. The compound of claim 2 wherein X is hydrogen.

4. The compounds of claim 2 wherein each alkyl group is of one to two carbons and X is hydrogen.

* * * * *